(12) United States Patent
McMinn

(10) Patent No.: US 9,700,417 B2
(45) Date of Patent: Jul. 11, 2017

(54) PROSTHESIS HAVING A LARGE FEMORAL HEAD

(71) Applicant: Derek James Wallace McMinn, Stourbridge West Midlands (GB)

(72) Inventor: Derek James Wallace McMinn, Stourbridge West Midlands (GB)

( * ) Notice: Subject to any disclaimer, the term of this patent is extended or adjusted under 35 U.S.C. 154(b) by 3 days.

(21) Appl. No.: 14/442,585

(22) PCT Filed: Jan. 24, 2014

(86) PCT No.: PCT/GB2014/050189
§ 371 (c)(1),
(2) Date: May 13, 2015

(87) PCT Pub. No.: WO2014/114944
PCT Pub. Date: Jul. 31, 2014

(65) Prior Publication Data
US 2016/0278928 A1    Sep. 29, 2016

(30) Foreign Application Priority Data

Jan. 25, 2013 (EP) .................................... 13275015

(51) Int. Cl.
*A61F 2/34* (2006.01)
*A61F 2/36* (2006.01)
*A61F 2/30* (2006.01)

(52) U.S. Cl.
CPC .............. *A61F 2/3609* (2013.01); *A61F 2/34* (2013.01); *A61F 2/36* (2013.01);
(Continued)

(58) Field of Classification Search
CPC .. A61F 2/36; A61F 2002/3625; A61F 2/3609; A61F 2/34
See application file for complete search history.

(56) References Cited

U.S. PATENT DOCUMENTS 5,037,438 A    8/1991  Davidson
5,405,394 A *  4/1995  Davidson ............. A61L 27/306
                                                   623/18.11
(Continued)

FOREIGN PATENT DOCUMENTS

EP    0562782 A2    9/1993
FR    2854320 A1   11/2004
(Continued)

OTHER PUBLICATIONS

PCT International Patent Application No. PCT/GB2014/050189, International Search Report mailed Feb. 27, 2014, 4 pages.
(Continued)

*Primary Examiner* — Jason-Dennis Stewart
(74) *Attorney, Agent, or Firm* — Morgan, Lewis & Bockius LLP

(57) ABSTRACT

A prosthesis comprises a femoral stem having a frustoconical femoral neck; a femoral head having an articular bearing surface with an outer diameter of 26 mm or more, and a frustoconically tapered internal recess; and a sleeve comprising a frustoconical body for insertion into the recess of the femoral head and a frustoconically tapered internal recess for receipt of the frustoconical femoral neck. A surface of the recess of the sleeve comprises oxidized zirconium or oxidized zirconium alloy to resist or minimize mechanically assisted crevice corrosion.

20 Claims, 3 Drawing Sheets

(52) U.S. Cl.
CPC ............... *A61F 2002/3035* (2013.01); *A61F 2002/30332* (2013.01); *A61F 2002/30474* (2013.01); *A61F 2002/365* (2013.01); *A61F 2230/0093* (2013.01); *A61F 2310/00239* (2013.01); *A61F 2310/00634* (2013.01)

(56) References Cited

U.S. PATENT DOCUMENTS

| | | | |
|---|---|---|---|
| 2002/0042656 A1 | 4/2002 | Hunter et al. | |
| 2005/0187638 A1 | 8/2005 | Glien et al. | |
| 2006/0188845 A1 | 8/2006 | Serafin et al. | |
| 2008/0058951 A1* | 3/2008 | Saladino | A61F 2/3609 623/23.24 |
| 2009/0306781 A1* | 12/2009 | Kyomoto | A61F 2/30767 623/18.11 |
| 2012/0203351 A1* | 8/2012 | Thompson | A61F 2/32 623/22.15 |

FOREIGN PATENT DOCUMENTS

| | | |
|---|---|---|
| GB | 2230192 A | 10/1990 |
| WO | 2005/027799 A1 | 3/2005 |
| WO | 2005/027799 A2 | 3/2005 |
| WO | 2012/035294 A2 | 3/2012 |
| WO | 2014/114944 A1 | 7/2014 |

OTHER PUBLICATIONS

Search Report issued in a corresponding United Kingdom Patent Application No. GB 1213250.2 dated Nov. 23, 2012.
International Search Report issued in a corresponding International Application No. PCT/GB2014/050189 dated Feb. 27, 2014.
Search Report issued in a corresponding European Application No. EP 13275015.9 dated Jun. 13, 2013.

* cited by examiner

PROSTHESIS HAVING A LARGE FEMORAL HEAD

This application is the U.S. national stage application of International (PCT) Patent Application Serial No. PCT/GB2014/050189, filed Jan. 24, 2014, which claims the benefit of EP Application No. 13275015.9, filed Jan. 25, 2013. The entire disclosure of each of these applications is hereby incorporated by reference.

FIELD OF THE INVENTION

The present invention relates to a prosthesis having a large femoral head such as may be used in a Total Hip Replacement (THR) procedure.

BACKGROUND TO THE INVENTION

A Total Hip Replacement (THR) involves replacement of both the acetabulum and the femoral head. Prosthesis for a total hip replacement thus consists of a femoral component and an acetabular cup. The femoral component comprises a femoral head (ball) which is attached to a femoral stem that is located in a patient's femur. The femoral component may be modular wherein separate femoral head and stem components are joined together. The stem commonly includes a tapered element, extending from a neck of the stem, for engagement in a complementary recess within the femoral head. This construction is desirable since it allows the head and stem portions to be made from different materials which are optimized for their particular function. Femoral stems are typically made of metals such as cobalt chromium, stainless steel and titanium alloy, which are cheap and resistant to scratching and fracture. Femoral heads may also be made from these materials, or they may be ceramic. For example, it is common to put a cobalt chromium head on a titanium alloy stem using most commonly a 12/14 mm neck taper.

Small femoral heads (typically having an outer diameter of 22 mm) were used in the first successful THR procedures pioneered by Sir John Charnley in the 1960's. At this time, femoral heads were generally metallic and the bearing surface of the acetabular cup was formed from conventional Ultra High Molecular Weight Polyethylene (UHMWP). Although small heads were found to have low wear against such conventional polyethylene cups, they had a high dislocation rate, which was reduced by the use of larger femoral heads (i.e. of 26 mm or more outer diameter). However, it was subsequently discovered that larger heads produced larger volumes of polyethylene debris, when articulating against conventional polyethylene, due to wear of the cup surface and such debris was thought to lead to observed tissue reactions and acetabular and femoral bone loss (known as osteolysis).

In the past 10 years, conventional polyethylene acetabular bearing surfaces have been abandoned in favour of cross-linked polyethylene to reduce cup wear in THRs.

Having largely conquered cup wear by a switch to cross-linked polyethylene, in the past 5 years surgeons have started using bigger and bigger femoral heads against cross-linked polyethylene to reduce the risk of dislocation discussed above in relation to small heads.

Over the past 2 years a new problem of accelerated severe taper corrosion and wear at the head/neck femoral junction has emerged leading to soft tissue reactions (known as pseudotumours).

It is therefore an object of the present invention to provide a femoral prosthesis with optimum characteristics to minimise the risk of pseudotumours and dislocation.

SUMMARY OF THE INVENTION

In accordance with a first aspect of the present invention, there is provided a prosthesis comprising: a femoral stem having a frustoconical femoral neck portion; a femoral head having an articular bearing surface with an outer diameter of 26 mm or more, and a frustoconically tapered internal recess; and a sleeve comprising a frustoconical body for insertion into the recess of the femoral head and a frustoconically tapered internal recess for receipt of the frustoconical femoral neck portion; wherein a surface of the recess of the sleeve comprises oxidised zirconium or oxidised zirconium alloy to resist or minimise mechanically assisted crevice corrosion.

The applicant believes that embodiments of the invention will provide a prosthesis which will be highly resistant to dislocation due the use of a large femoral head but without the current disadvantage of corrosion at the head/neck taper due to the presence of a sleeve having at least an internal surface comprising oxidised zirconium or oxidised zirconium alloy. Accordingly, the risk of pseudotumours associated with using large heads articulating against cross-linked polyethylene or metal cups will be reduced.

It was originally thought that pseudotumours were exclusively observed when metal-on-metal THRs (i.e. having metal heads bearing on metal cups) failed. However, this effect has now also been observed in THRs with cross-linked polyethylene cups and heads of 26 mm diameter or more as well as in metal-on-metal THRs with head sizes of 36 mm or greater.

On investigating the current problem of head/neck taper corrosion, the applicant has located a paper by Goldberg (Goldberg J R, Gilbert J L, Jacobs J J et al: A Multicenter Retrieval Study of the Taper Interfaces of Modular Hip Prosthesis; Clinical Orthopaedics 2002; 401:149-161) in which mechanically-assisted crevice corrosion was observed on retrieved head and neck tapers regardless of whether similar or mixed alloy heads and necks were employed. This study suggested that increasing the neck diameter will increase the neck stiffness and this may reduce fretting and subsequent corrosion of the taper interface. However, these findings do not appear to have been considered as clinically significant and no further developments have been made in this area.

In an unrelated paper it has been observed that highly cross-linked polyethylene increases the frictional torque between the femoral head and acetabular liner upon articulation (by approximately a factor of two when compared to conventional polyethylene). Furthermore, this effect has been found to be greater with increasing head size (Burroughs B R, Muratoglu O K, Bragdon C R et al: In vitro comparison of frictional torque and torsional resistance of aged conventional gamma-in-nitrogen sterilized polyethylene versus aged highly crosslinked polyethylene articulating against head sizes larger than 32 mm; Acta Orthopaedica 2006; 77 (5): 710-718).

The applicant therefore believes that corrosion at the head/neck junction is less a function of the materials employed for the head and the neck and more a function of the stresses placed upon the junction, for example, as a result of the frictional torque resulting from the acetabular bearing surface and the size of the femoral head.

Embodiments of the present invention therefore set out to solve the problem of mechanically-assisted crevice corrosion which results from the use of large heads which generate high frictional torque with their associated cups. As described above, a prosthesis having a large femoral head can result in severe mechanically assisted crevice corrosion with a femoral neck regardless of whether the head and neck are of the same or different materials. Although the prior art suggested solving this problem using an increased neck diameter, this would have the disadvantage of increasing impingement between the femoral neck and the acetabular cup edge as a result of reducing the head to neck ratio.

Instead, the applicant has surprisingly found that the use of a sleeve is advantageous in solving this problem even though the use of a sleeve may, at first, appear counter-intuitive since we are trying to reduce the mechanically induced corrosion at a material interface and introducing a sleeve results in two different material interfaces instead of just one, thereby increasing the mechanical complexity of the prosthesis and providing further surfaces where corrosion can occur. However, the applicant has discovered that mechanically-assisted corrosion is not, in practice, a common problem at the interface between the sleeve and the head but is only really problematic between the sleeve and the neck. The applicant has also discovered that by providing oxidised zirconium or oxidised zirconium alloy in the sleeve recess, the mechanically-assisted crevice corrosion can be prevented or at least reduced. The applicant believes that this may be because any corrosion to the surface of the sleeve recess will simply result in re-oxidation of the oxidised zirconium or oxidised zirconium alloy, which will not have a significant effect on the material characteristics.

The phrase 'oxidised zirconium or zirconium alloy' will be understood to mean oxidised zirconium or oxidised zirconium alloy throughout.

Zirconium has been known to be corrosion-resistant for many years. Oxidised zirconium or zirconium alloy, also referred to as zirconium oxide (the stable form of which is zirconium dioxide), is a ceramic material which is hard, low-friction, highly wear-resistant and biocompatible. It is therefore ideal for use in implants and other medical devices.

In addition, the use of a sleeve according to the invention allows the large femoral heads to be made out of traditional materials such as cobalt chrome or ceramic, which are relatively cheap to make and are generally resistant to scratching in the event of any dislocation. The use of sleeves in THRs also gives the advantage that a smaller femoral head inventory can be stocked, since a range of sleeve lengths can be provided.

It will be understood that in accordance with standard practice, the sleeve will be configured for a tight frictional fit onto the tapered neck of the femoral stem and a similar frictional fit within the head recess.

Embodiments of the present invention may be particularly advantageous in the following situations since each of them is likely to result in high stress and increased torque at the head/neck junction: 1) where the acetabular cup bearing material contains cross-linked polyethylene; 2) where a metal-on-metal bearing is employed; and 3) where the head centre is deliberately offset from the centre line of the neck (e.g. as described in the applicant's WO2012/035294). In each case, a large femoral head having an outer diameter of 26 mm or more is likely to be employed.

Thus, in embodiments of the invention, the prosthesis may further comprise an acetabular cup having a cross-linked polymer bearing surface. Alternatively, the prosthesis may further comprise an acetabular cup having a metal bearing surface.

The frustoconical femoral neck portion may have a central longitudinal axis that is offset with respect to a centre of the femoral head, when assembled thereon via the sleeve. Accordingly, the sleeve may be asymmetrical such that the axis of rotation of the internal recess is parallel to but off-set from a central longitudinal axis of the frustoconical body. Accordingly, the body of the sleeve may be thicker on one side of the recess when compared to the opposite side of the recess. Alternatively, the head recess may have a central longitudinal axis that is offset with respect to the centre of the femoral head.

The body may be constituted by a collar. The sleeve recess may be constituted by a passageway extending through the body from one side to another.

Alternatively, the body may have a closed end such that the sleeve recess extends only part way through the body.

In some embodiments, the whole of the surface of the body comprises oxidised zirconium or zirconium alloy. In other embodiments, only portions of the surface of the body of the sleeve comprise oxidised zirconium or zirconium alloy, such as the portions which come into contact with the neck and head, during use. Thus, the surface of the internal recess and the external surface of the body may comprise oxidised zirconium or zirconium alloy. In particular embodiments, the sleeve may only comprise oxidised zirconium or zirconium alloy on the surface of the internal recess.

In some embodiments, a layer of oxidised zirconium or zirconium alloy is provided by a coating applied to at least a surface of the recess of the frustoconical body. The use of a coating allows the body of the sleeve to be made from one or more materials selected according to their particular physical properties, such as weight, cost, strength or durability, while corrosion resistance is provided by the oxidised zirconium or zirconium alloy coating. For example, the body of the sleeve may be made from a metal or metal alloy such as titanium or cobalt-chromium. The coating may be applied by methods known to those skilled in the art, such as physical vapour deposition (PVD). A coating of oxidised zirconium or zirconium alloy may be applied to the body of the sleeve. Alternatively, a coating of non-oxidised zirconium or zirconium alloy may be applied to the body followed by oxidation of the zirconium or zirconium alloy in situ.

Alternatively, the frustoconical body may be formed entirely or partly from zirconium or zirconium alloy. In some embodiments, the frustoconical body may be a composite comprising an outer portion of zirconium or zirconium alloy and an inner core of a different material, such as titanium or cobalt-chromium. The body may be cast or machined by conventional methods to the desired shape and size of the sleeve. The body may then be subjected to conditions which cause oxidation of the zirconium or zirconium alloy at the surface of the body, resulting in the formation of a portion (e.g. layer) of a hard, corrosion-resistant oxidised zirconium or zirconium alloy which is integral with the body. It will be appreciated that there may not necessarily be a distinct boundary between the oxidised surface and the non-oxidised body of the sleeve, due to the diffusion of oxygen from the oxidation process into the body. The advantage of an oxidised zirconium or zirconium alloy portion or layer which is integral with the body of the sleeve over coatings is that coatings can detach from the body under high stress. Detachment of an oxidised zirconium or zirconium alloy surface has never been described in use.

Methods of forming oxidised zirconium or zirconium alloy surfaces are well documented and will be known to those skilled in the art. Such methods are described by U.S. Pat. No. 2,987,352, U.S. Pat. No. 5,037,438, U.S. Pat. No. 4,671,824 and WO98/42390, the contents of which are incorporated herein by reference.

As used herein, "zirconium alloy" is defined as any metal alloy containing zirconium in an amount greater than zero. In some embodiments, the alloy comprises at least 50%, at least 70%, at least 80%, at least 85%, at least 90%, at least 95% or at least 97% zirconium. The zirconium alloy may comprise one or more alloying elements selected from oxygen, tin, niobium, titanium, hafnium and yttrium. In a particular embodiment, the zirconium alloy may be Zr-2.5Nb, which is an alloy of zirconium, niobium and oxygen. Suitable commercial alloys include ZIRCADYNE 705, ZIRCADYNE 702 and Zircaloy.

There are many forms of oxidised zirconium, including white, beige and black or blue-black. In some embodiments, the oxidised zirconium or zirconium alloy is the blue-black or black form.

The portion of oxidised zirconium or zirconium alloy may have a thickness of from 1 to 40 μm, from 1 to 30 μm from 1 to 20 μm, from 2 to 10 μm, or from 3 to 7 μm.

In some embodiments, the surface of the internal recess and/or the external surface of the body comprises an anti-rotational element configured to resist rotational movement between the sleeve and an inter-engaging part (e.g. neck or head), in use.

It is believed that when prosthetic implants encounter a high level of frictional torque at a bearing surface this can give rise to small rotational movements between other inter-engaging parts of the prosthesis, which can cause wear and corrosion. Thus, in addition to the effect of the oxidised zirconium or zirconium on the surface of the sleeve recess, the provision of an anti-rotational element configured to resist rotational movement between the neck and sleeve also helps to minimise wear and corrosion at the head/neck taper junction by increasing the resistance to rotational torque. In some embodiments, the anti-rotational element comprises one or more planar surfaces or longitudinal ridges, grooves or splines. Prosthetic components comprising such anti-rotational elements are described in the Applicant's co-pending application WO2012/035294.

Notably, the femoral stem and the femoral head may comprise any desired materials and each may be made from the same or different materials. In certain embodiments, the femoral stem may comprise metal such as cobalt chromium, stainless steel or titanium alloy. Similarly, the femoral head may comprise metal such as cobalt chromium, stainless steel or titanium alloy or the femoral head may comprise ceramic. More specifically, the femoral head may comprise a metal or ceramic articular bearing surface. In a particular embodiment, the femoral head may comprise cobalt chromium and the femoral stem may comprise titanium alloy. Alternatively, the femoral head may be formed from PEEK. Such a PEEK femoral head could be used with an acetabular cup having a cross-linked, non-cross-linked, or partially cross-linked polyethylene bearing surface. It could also be used in conjunction with a metal cup bearing. While wear might otherwise occur between the PEEK material and the and the frustoconical neck, the provision of an oxidized zirconium or zirconium alloy, as described herein, can reduce or prevent this.

In embodiments of the invention, where the sleeve is formed entirely from oxidised zirconium or oxidised zirconium alloy, for example, the sleeve may be fixed into the recess of the femoral head, prior to insertion of the frustoconical neck of the stem. The oxidised zirconium or zirconium alloy may be moulded or heat pressed into the recess in the femoral head. A thin layer of such oxidised zirconium or zirconium alloy material may form the sleeve, which is then fixed into the recess of the head. Fixation features may be added to facilitate locking of the PEEK head to the oxidised zirconium/alloy taper surface. These may comprise a porous surface to the oxidised zirconium/alloy, or recesses, for example. This inner oxidised zirconium or zirconium alloy surface could then directly lock onto the taper of the frustoconical femoral neck.

The femoral head may have an outer diameter in the range of 26 mm to 62 mm or more. In particular, the femoral head may have an outer diameter of at least 26, 28, 32, 36, 38, 40, 42, 44, 46, 48, 50, 52, 54, 56, 58, 60 or 62 mm.

The femoral neck portion and sleeve recess may comprise a 12/14 mm taper or any other suitable dimensions.

A second aspect of the present invention relates to the use of a sleeve in a prosthesis comprising a femoral stem and a femoral head having an articular bearing surface with an outer diameter of 26 mm or more; the sleeve comprising a frustoconical body having a frustoconically tapered internal recess, wherein a surface of the recess of the sleeve comprises oxidised zirconium or oxidised zirconium alloy to resist or minimise mechanically assisted crevice corrosion.

A third aspect of the invention provides a prosthesis comprising a femoral stem having a frustoconical femoral neck, a femoral head having an articular bearing surface, and a frustoconically tapered internal recess, wherein a surface of the recess of the head comprises oxidised zirconium or oxidised zirconium alloy to resist or minimise mechanically assisted crevice corrosion.

The femoral head may have an outer diameter of 26 mm or more. The femoral head may be formed partially or completely from formed from PEEK. The oxidised zirconium/alloy layer may be moulded into the internal recess of the PEEK head. Alternatively, the oxidised zirconium/alloy taper surface may be heat pressed into the recess of the head.

As above, fixation features may be added to facilitate locking of the PEEK head to the oxidised zirconium/alloy taper surface. These may comprise a porous surface to the oxidised zirconium/alloy or recesses, for example. This inner oxidised zirconium/alloy surface could then directly lock onto the taper of the frustoconical femoral neck.

Again, such a PEEK femoral head could be used with a cross-linked, non-cross-linked, or partially cross-linked polyethylene acetabular cup. It could also be used in conjunction with a metal cup bearing. While wear might otherwise occur between the PEEK material and the and the frustoconical neck, the provision of an oxidized zirconium or alloy thereof, as described herein, can reduce or prevent this.

The sleeve of the first aspect may additionally be used with this aspect of the invention.

BRIEF DESCRIPTION OF THE DRAWINGS

Embodiments of the present invention will now be described with reference to the accompanying Figures in which.

DETAILED DESCRIPTION OF CERTAIN EMBODIMENTS

Figures 1A, 1B:
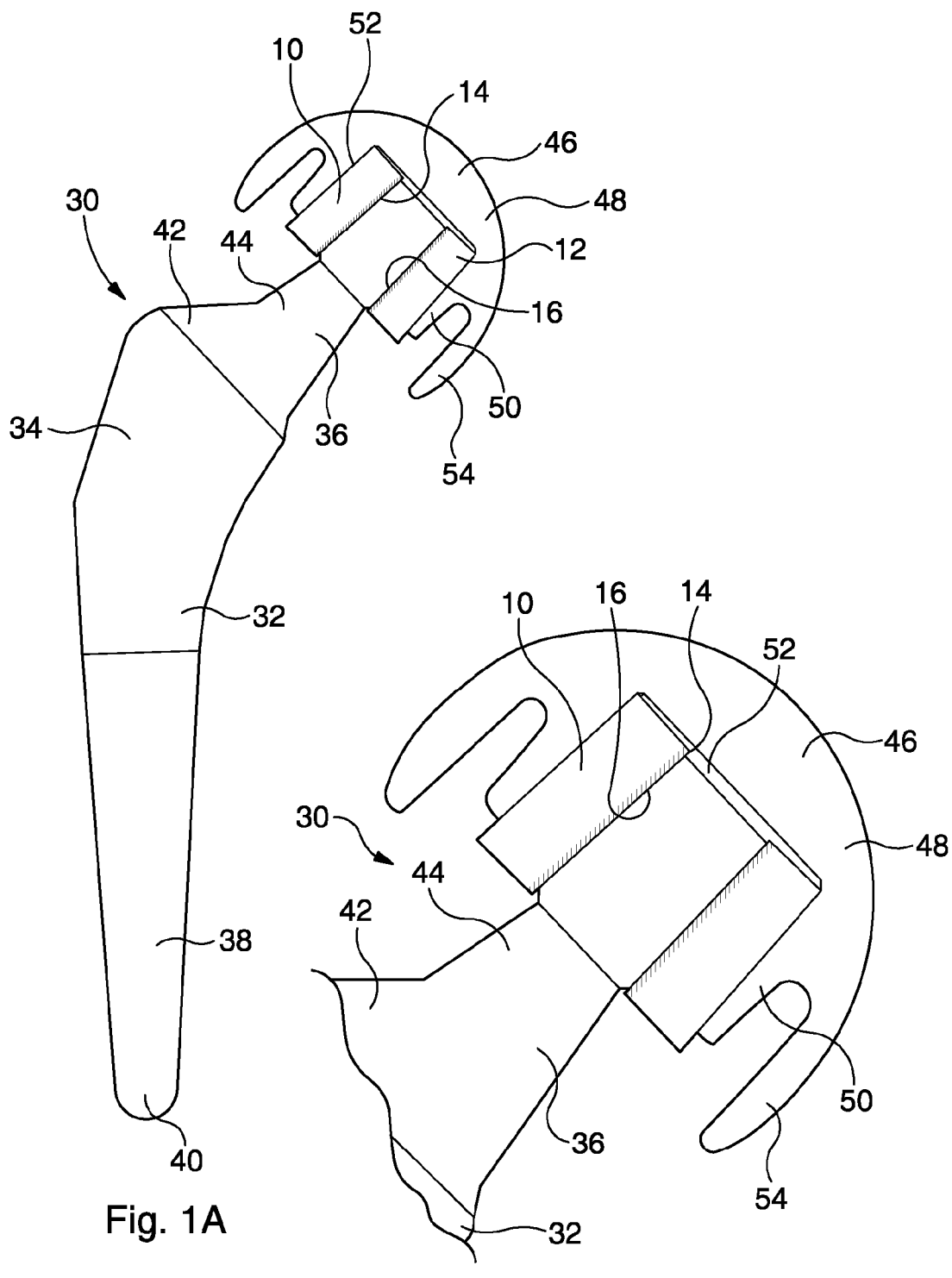
FIGS. 1A and 1B show a side cross-sectional view of a THR prosthesis comprising a prosthetic sleeve engaged with a femoral head and a femoral stem in accordance with an embodiment of the present invention.

With reference to FIGS. 1A and 1B, there is illustrated a prosthesis 30 for a THR procedure. The prosthesis 30 comprises a femoral stem 32, a femoral head 46 and a sleeve 10.

The femoral stem 32 comprises a shoulder 34, a neck 36 and a leg 38. The shoulder 34 has a slightly curved form, tapering inwardly in a distal direction to the most proximal end of the leg 38. The leg 38 comprises a straight elongate conical section tapering inwardly in a distal direction and terminating in a rounded tip 40. The neck 36 extends from the widest and most proximal end of the shoulder 34 and comprises a base 42 and a frustoconical femoral neck portion constituted by a cone 44. The base 42 tapers more in a lateral direction than in a proximal direction, while the cone 44 comprises a frustoconical taper extending in a proximal-lateral direction.

The sleeve 10 comprises a frustoconical body 12 having a substantially frustoconically tapering internal recess 14. A surface 16 of the recess 14 comprises oxidised zirconium or oxidised zirconium alloy to resist or minimise mechanically assisted crevice corrosion. In use, the free end of the cone 44 of the neck 36 is received in the tapered internal recess 14 of the sleeve 10.

The femoral head 46 comprises a part-spherical articular bearing surface 48 (for location within a corresponding acetabular cup, not shown), and an integral support 50 having a substantially frustoconically tapered recess 52 into which the sleeve 10 is received. In this embodiment, the articular bearing surface 48 has with an outer diameter of 26 mm or more, constituting a so-called 'large' femoral head. In the embodiment shown, the head 46 includes a skirt 54 depending from the bearing surface 48. The skirt 54 is spaced from the support 50 to allow the skirt 54 to be placed over a portion of a patient's resected femur to locate the head 46 thereon.

The sleeve 10 comprising the surface 16 of oxidised zirconium or zirconium alloy thus acts to reduce corrosion at the junction between the tapered cone 44 of the neck 36 and the internal tapered recess 14 of the sleeve 10, while allowing the neck 36 and head 46 to be made out of traditional materials.

Figure 2A:
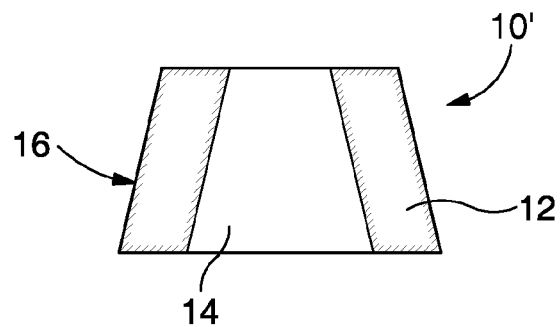
FIG. 2A shows a longitudinal cross-sectional view of an alternative prosthetic sleeve for use with the prosthesis of FIGS. 1A and 1B.

An alternative sleeve 10' is shown in FIG. 2A in which the body 12 is made entirely of zirconium or a zirconium alloy and the entire surface 16 of the sleeve 10' comprises oxidised zirconium or a zirconium alloy which is continuous and contiguous with the body 12.

Figure 2B:
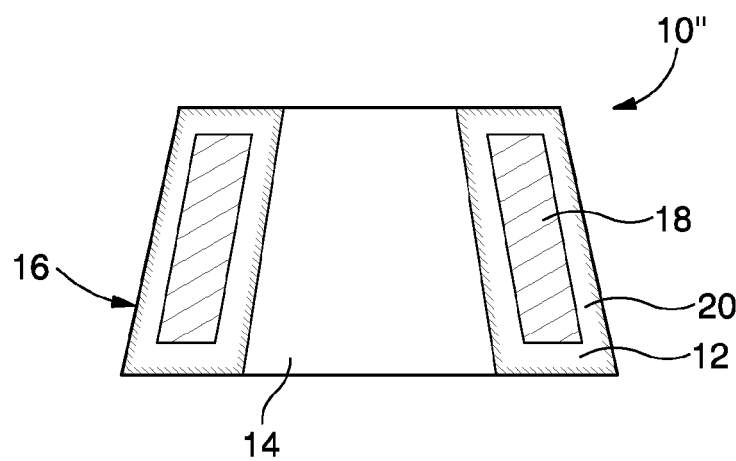
FIG. 2B shows a longitudinal cross-sectional view of a further prosthetic sleeve for use with the prosthesis of FIGS. 1A and 1B.

A further sleeve 10" is shown in FIG. 2B in which the body 12 is a composite comprising an inner core 18 of a metal such as titanium or cobalt-chromium, and an outer layer 20 of zirconium or zirconium alloy. As illustrated, the entire surface 16 of the sleeve 10" comprises a oxidised zirconium or a zirconium alloy 16 which is continuous and contiguous with the outer layer 20.

Figure 2C:
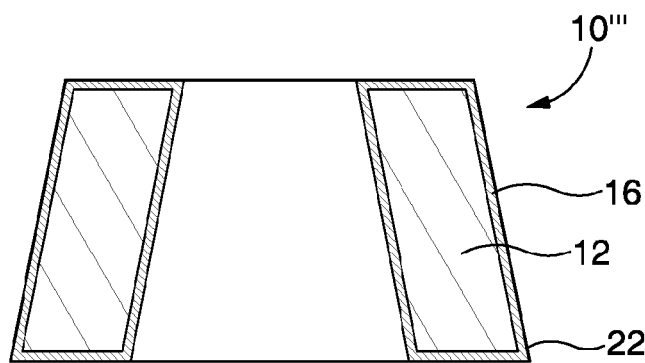
FIG. 2C shows a longitudinal cross-sectional view of another prosthetic sleeve for use with the prosthesis of FIGS. 1A and 1B.

Another sleeve 10''' is shown in FIG. 2C in which the body 12 is formed from a non-zirconium material such as titanium or cobalt-chromium. In this case, the entire surface 16 of oxidised zirconium or zirconium alloy is constituted by a coating 22 which is applied to the surface of the body 12.

Figure 3:
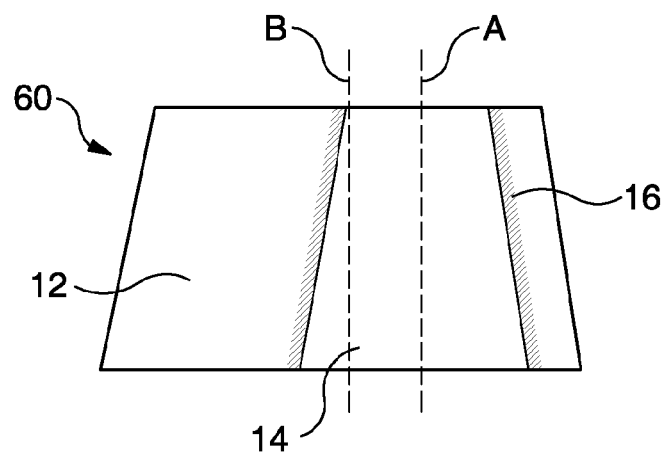
FIG. 3 shows a longitudinal cross-sectional view of an offset prosthetic sleeve for use with the prosthesis of FIGS. 1A and 1B.

FIG. 3 shows a longitudinal cross-sectional view of an offset prosthetic sleeve 60 for use with the prosthesis 30 of FIGS. 1A and 1B. In this embodiment, only a surface 16 of the recess 14 comprises oxidised zirconium or oxidised zirconium alloy and a axis A of rotation of the recess 14 is parallel to but off-set from a central longitudinal axis B of the frustoconical body 12. This arrangement allows the position of the head 46 to be altered with respect to the neck 36 by the surgeon rotating the sleeve 60 relative to the neck 36.

Figure 4:
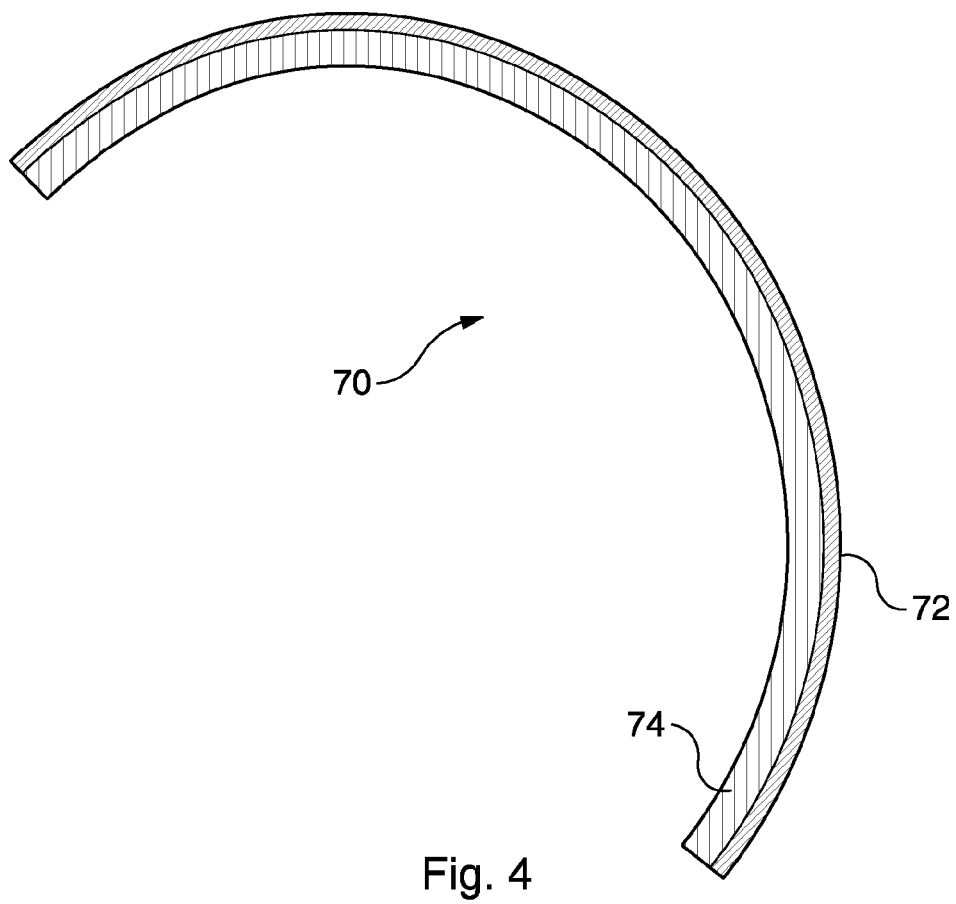
FIG. 4 shows a cross-sectional view of an acetabular cup for use with the prosthesis of FIGS. 1A and 1B.

FIG. 4 shows a cross-sectional view of an acetabular cup 70 for use with the prosthesis 30 of FIGS. 1A and 1B. The acetabular cup 70 comprises a hemi-spherical metal outer shell 72 and a hemispherical polymer liner 74 wherein at least a portion of the surface of the liner 74 comprises crosslinked polyethylene to minimise wear of the cup. Where the prosthesis 30 is used in a metal-on-metal bearing, the entire surface of the cup 70 will be metal.

In an alternative embodiment, in which only changes to the embodiment described above will be discussed, the femoral head is formed from PEEK, and the sleeve is formed from oxidised zirconium or zirconium alloy which is fixed into the frustoconical recess of the head, prior to the neck being inserted. The oxidised zirconium or zirconium alloy layer is, in the present embodiment, heat pressed into the recess, but could also be moulded into the recess. On the surface of the oxidised zirconium or zirconium alloy layer facing the femoral head, a porous surface is provided to facilitate locking of the PEEK to the oxidised zirconium or zirconium alloy surface. Alternatively, recesses can be formed into the oxidised zirconium or zirconium alloy to achieve the same effect. The corresponding frustoconical neck of the femoral stem is then inserted into the recess of the head to form the prosthesis.

It will be appreciated by persons skilled in the art that various modifications may be made to the above embodiments without departing from the scope of the present invention. For example, features described in relation to one embodiment may be mixed and matched with features described in relation to one or more other embodiments.

The invention claimed is:

1. A prosthesis (30) comprising:
    a femoral stem (32) having a frustoconical femoral neck (44);
    a femoral head (46) having an articular bearing surface (48) with an outer diameter of 26 mm or more, and a frustoconically tapered internal recess (52); and
    a sleeve (10) comprising a frustoconical body (12) for insertion into the recess (52) of the femoral head (46) and a frustoconically tapered internal recess (14) for receipt of the frustoconical femoral neck (44);
    wherein the sleeve is uncoated and formed entirely of a metal, the metal being zirconium or a zirconium alloy with one or more additional metals.

2. The prosthesis according to claim 1 further comprising an acetabular cup (70) having a cross-linked polymer bearing surface (74).

3. The prosthesis according to claim 1 further comprising an acetabular cup (70) having a metal bearing surface.

4. The prosthesis according to claim 1 wherein the frustoconical femoral neck (44) has a central longitudinal axis which is offset with respect to a centre of the femoral head (46), when assembled thereon via the sleeve (10).

5. The prosthesis according to claim 4 wherein the sleeve (60) is asymmetrical such that the axis of rotation (A) of the sleeve recess (14) is parallel to but off-set from a central longitudinal axis (B) of the frustoconical body (12).

6. The prosthesis according to claim 4 wherein the head recess (52) has a central longitudinal axis that is offset with respect to the centre of the femoral head (46).

7. The prosthesis according to claim 1 wherein the surface (16) of the sleeve (10) recess (14) and/or the external surface of the body (12) comprises an anti-rotational element configured to resist rotational movement between the sleeve (10) and the neck (44) and/or head (46), in use.

8. The prosthesis according to claim 1 wherein the sleeve is formed entirely of zirconium.

9. The prosthesis according to claim 1 wherein the sleeve is formed entirely of the zirconium alloy with one or more additional metals, the one or more additional metals comprising niobium.

10. The prosthesis according to claim 1 wherein the sleeve is formed entirely of the zirconium alloy with one or more additional metals, the one or more additional metals comprising tin.

11. The prosthesis according to claim 1 wherein the sleeve is formed entirely of the zirconium alloy with one or more additional metals, the one or more additional metals comprising titanium.

12. The prosthesis according to claim 1 wherein the sleeve is formed entirely of the zirconium alloy with one or more additional metals, the one or more additional metals comprising hafnium.

13. The prosthesis according to claim 1 wherein the sleeve is formed entirely of the zirconium alloy with one or more additional metals, the one or more additional metals comprising yttrium.

14. Use of a sleeve (10) in a prosthesis (30) comprising a femoral stem (32) and a femoral head (46) having an articular bearing surface (48) with an outer diameter of 26 mm or more; the sleeve (10) comprising a frustoconical body (12) having a frustoconically tapered internal recess (14), wherein the sleeve is uncoated and formed entirely of a metal, the metal being zirconium or a zirconium alloy with one or more additional metals.

15. The use according to claim 14 wherein the sleeve is formed entirely of zirconium.

16. The use according to claim 14 wherein the sleeve is formed entirely of the zirconium alloy with one or more additional metals, the one or more additional metals comprising niobium.

17. The use according to claim 14 wherein the sleeve is formed entirely of the zirconium alloy with one or more additional metals, the one or more additional metals comprising tin.

18. The use according to claim 14 wherein the sleeve is formed entirely of the zirconium alloy with one or more additional metals, the one or more additional metals comprising titanium.

19. The use according to claim 14 wherein the sleeve is formed entirely of the zirconium alloy with one or more additional metals, the one or more additional metals comprising hafnium.

20. The use according to claim 14 wherein the sleeve is formed entirely of the zirconium alloy with one or more additional metals, the one or more additional metals comprising yttrium.

* * * * *